(12) United States Patent
Cappellini

(10) Patent No.: US 12,171,644 B2
(45) Date of Patent: Dec. 24, 2024

(54) SYSTEM AND METHOD FOR MAKING ELASTIC PANELS

(71) Applicant: FIRST QUALITY BABY PRODUCTS, LLC, Great Neck, NY (US)

(72) Inventor: Pierluigi Cappellini, Bellefonte, PA (US)

(73) Assignee: FIRST QUALITY BABY PRODUCTS, LLC, Great Neck, NY (US)

( * ) Notice: Subject to any disclaimer, the term of this patent is extended or adjusted under 35 U.S.C. 154(b) by 0 days.

(21) Appl. No.: 18/126,116

(22) Filed: Mar. 24, 2023

(65) Prior Publication Data

US 2023/0225908 A1 Jul. 20, 2023

Related U.S. Application Data

(62) Division of application No. 17/394,713, filed on Aug. 5, 2021, now Pat. No. 11,617,686.

(60) Provisional application No. 63/061,240, filed on Aug. 5, 2020.

(51) Int. Cl.
*A61F 13/15* (2006.01)
(52) U.S. Cl.
CPC .. *A61F 13/15593* (2013.01); *A61F 13/15747* (2013.01); *A61F 13/15772* (2013.01); *A61F 2013/1578* (2013.01); *A61F 2013/15869* (2013.01); *A61F 2013/1591* (2013.01)

(58) Field of Classification Search
CPC .......... A61F 13/15593; A61F 13/15747; A61F 13/15772; A61F 2013/1578; A61F 2013/15869; A61F 2013/1591
See application file for complete search history.

(56) References Cited

U.S. PATENT DOCUMENTS

| 4,900,384 A * | 2/1990 | Sanders | A61F 13/15593 |
| | | | 604/385.27 |
| 2019/0231606 A1 * | 8/2019 | Andrews | B29C 65/08 |

* cited by examiner

*Primary Examiner* — Vishal I Patel
(74) *Attorney, Agent, or Firm* — Amster, Rothstein & Ebenstein LLP

(57) ABSTRACT

A system for manufacturing elastic strand nonwoven panels including an unwind module, a lamination module and a folding module. Elastic strand material is fed from cores disposed on the unwind module through rollers towards the lamination module, where the elastic strand material is attached to a nonwoven web to form an elastic strand nonwoven web. At the folding module, the elastic strand nonwoven web is folded over itself by operation of plates underneath which the elastic strand nonwoven web is fed under tension.

4 Claims, 11 Drawing Sheets

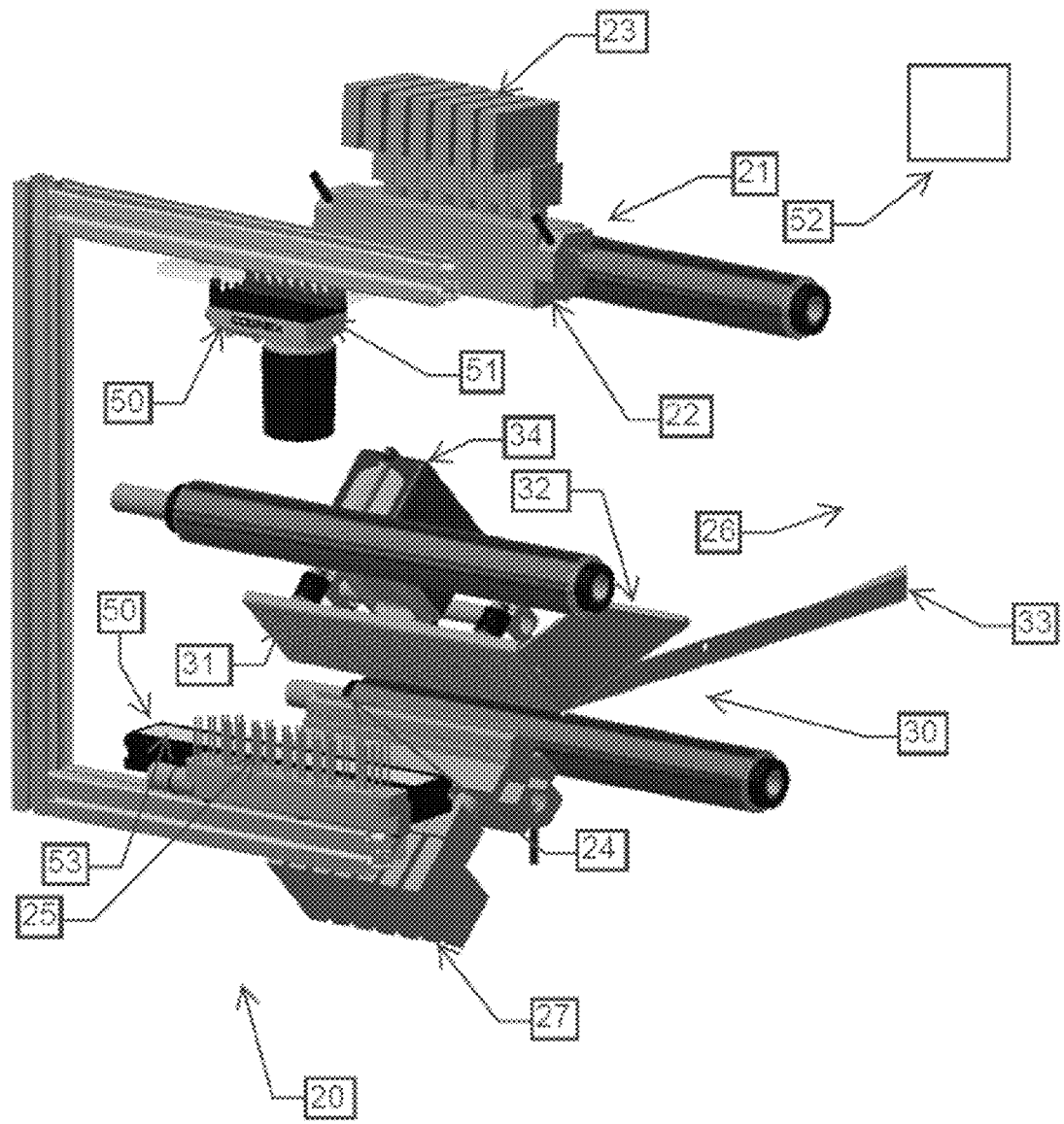

FIGURE 6A
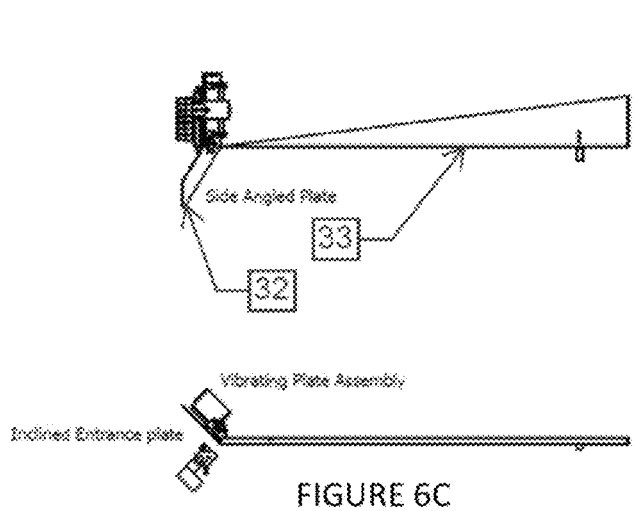
FIGURE 6B
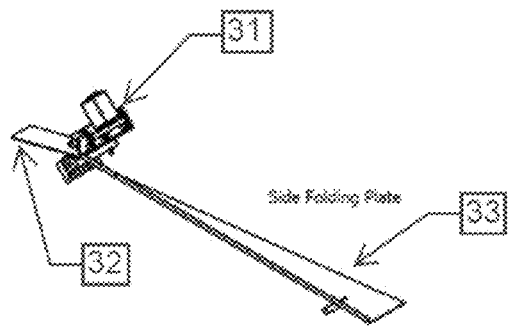
FIGURE 6C
FIGURE 7 A
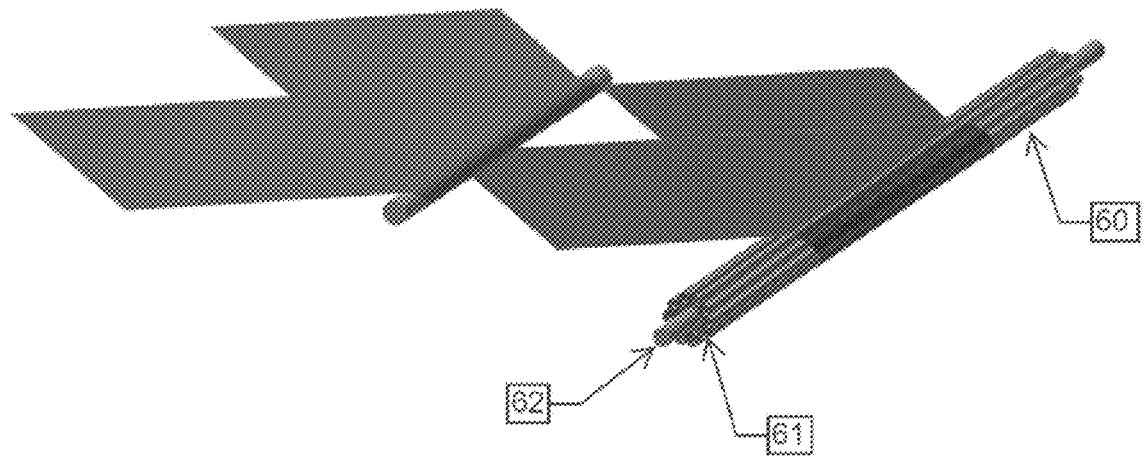

# SYSTEM AND METHOD FOR MAKING ELASTIC PANELS

CROSS-REFERENCE TO RELATED APPLICATIONS

This application is a divisional based on U.S. patent application Ser. No. 17/394,713, filed Aug. 5, 2021 and entitled SYSTEM AND METHOD FOR MAKING ELASTIC PANELS, which in turn claims the benefit of and priority to U.S. Provisional Patent Application No. 63/061,240, filed Aug. 5, 2020, the contents of which are herein incorporated by reference in their entirety into the present application.

FIELD OF THE INVENTION

The present invention generally relates to elastic panels for diapers and methods of making the same.

BACKGROUND

Disposable diapers have been manufactured and sold for over fifteen years. As products evolved, the use of elastic panels developed for comfort and flexibility. For example, elastic panels are often used in a waist portion of a diaper. Elastic panels sometimes include an elastic film layer laminated between outer layers of inelastic material, such as a nonwoven material. It is also known to use elastic strands to make elastic panels. The elastic strands may be attached to a material such as a nonwoven using an adhesive in a lamination module. Ultrasonic bonding is also sometimes utilized to retain elastic strands in the panels.

One problem associated with current processes for making elastic panels relates to the unwinding of elastic strands. It is common to have multiple tree-like stands on the floor adjacent a diaper manufacturing line. Each stand holds multiple cores of elastic strands. The elastic strands are pulled off the cores and fed over yarn guide rollers through a circuitous route to a lamination module. The elastic strands are held under tension which is monitored via tension sensors, but the elastic strand yarn guide rollers and tension sensors create friction, which negatively affects the overall tension, which in turn results in breakage of the elastic strands. When an elastic strand breaks, a machine operator must find the broken strand, string it through the circuitous route (sometimes having to physically enter the machine) and re-start the machine. This operation may take from 20 to 30 minutes. This issue is magnified when a product/process requires a high count of elastic strands feeding into a lamination process. Accordingly, there is a need for improved elastic unwind modules.

U.S. Pat. No. 7,905,446 teaches elastic cores positioned on a creel having multiple spool holders. Despite the teaching of the patent, there is a continuing need for improved elastic unwind modules.

Another problem associated with current processes for making elastic panels relates to the application of adhesive. It is common to use hot melt adhesives in the formation of elastic panels. The adhesive is heated in a vessel and flows through a heated glue head to the nonwoven. When a portion of a nonwoven web needs to be folded over, the nonwoven travels over a bar or plate, which creates friction and heat. Lighter basis weight nonwoven webs can be porous, which may result in bleed-through of the adhesive (the adhesive passes through the nonwoven and some of it comes out the side opposite of where the adhesive was applied). The process necessitates cooling of the adhesive after application to the nonwoven and attachment of the elastic strands. It is common for the glue to spill over the edges of the nonwoven, creating pools of adhesive on or around the lamination module. The cooling requires chilled water which increases operating costs and the water may leak, leading to problems in the lamination process. Therefore, there is need for an improved elastic panel lamination module to address these issues.

During the process of making elastic panels, it is common for elastic strands to break. It is frequently difficult to identify which elastic strand broke and re-string it. There is a need for a way to quickly detect a broken elastic strand.

Another problem associated with processes for making elastic panels relates to the floor space required for elastic unwinds, lamination modules and folding modules. In one nonwoven converting process, the nonwoven webs are processed parallel and in line to the converting line. This setup requires a multitude of elastic strands to be fed from un-winding stands, generally placed outward of the converting equipment. The configuration requires a convoluted elastic strand feeding including multiple un-winder stands and routing through a multitude of rollers into the lamination process. Alternative elastic panel lamination modules may feed a diaper machine in the cross direction, necessitating rotating the panels in the diaper manufacturing machine. There is a need to reduce floor space required for diaper manufacturing machines and associated modules.

SUMMARY OF THE INVENTION

The present invention provides a elastic unwind module including a modular system that can be expanded based on requirements. A unwind module includes a core stand; motor driven rollers; a pressure roller that rests upon the motor driven rollers; and a yarn guide roller oriented such that it turns an elastic strand 90° relative to a cross direction of the module and attached on a pivot point. In order to achieve an optimal web path, the strands may be fed side by side, parallel, and with the same path as a finished elastic panel laminate.

A lamination module including means for feeding a nonwoven to the module; means for applying adhesive to the nonwoven; means for feeding elastic strands to the module; and a folding module including a vibrating inclined folding plate, a side angle plate and a folding plate. The module may further include means for aligning elastic strands and/or means for observing the elastic strands. Means for feeding a second nonwoven to the module may also be provided.

A vision system for identifying broken and/or missing elastic strands includes a camera, a light, a monitor and a computer connected to the camera and programmed to detect broken strands.

A method for making an elastic panel includes feeding a nonwoven and elastic strands to a lamination module including means for applying an adhesive to the nonwoven and the elastic strands; and a folding module including a vibrating inclined folding plate, a side angle plate and a folding plate; applying the adhesive to coat the nonwoven and the elastic strands; applying the elastic strands to the adhesive coated nonwoven to create an elastic strand nonwoven and folding the elastic strand nonwoven over to make an elastic strand panel.

A method for making an elastic panel includes feeding a nonwoven and elastic strands to a lamination module including means for bonding the nonwoven in areas where adhesive coated elastic strands are not present; a folding module` including a vibrating inclined folding plate, a side angled plate and a folding plate; applying adhesive to each elastic strand prior to contacting the nonwoven; and folding the nonwoven over, to make an elastic strand panel, wherein the means for bonding the nonwoven are selected from the group consisting of applying an adhesive and utilizing ultrasonic bonding.

A separate method for making an elastic panel includes feeding a first nonwoven and elastic strands to a lamination module including means for applying an adhesive to the nonwoven and the elastic strands; and a folding module including a vibrating inclined folding plate, a side angle plate and a folding plate; applying the adhesive to coat the nonwoven and the elastic strands; applying the elastic strands to the adhesive coated nonwoven to create an elastic strand nonwoven; feeding a second nonwoven to the lamination module and laminating the second nonwoven over the elastic strand nonwoven to create an elastic strand panel.

A turn bar includes at least two adjacent rods connected to a center axis. The rods can be driven around a common center axis and by a common motor. The turn bar may additionally include a motor to provide traversing motion.

According to an exemplary embodiment of the present invention, a system for manufacturing elastic strand nonwoven panels comprises: an unwind module comprising: a first frame member that supports one or more cores of elastic strand material; a second frame member that supports one or more rollers through which the elastic strand material is fed from the one or more cores; and a third frame member that supports one or more guide rollers that angle the elastic strand material away from the unwind module; a lamination module comprising: a first input point through which the elastic strand material is guided from the one or more guide rollers of the unwind module; a second input point through which at least one nonwoven web is guided; and a lamination device that attaches the elastic strand material to the at least one nonwoven web to form an elastic strand nonwoven web; and a folding module comprising: a first plate; a second plate attached to and extending at an angle relative to the first plate; and a third plate extending substantially parallel to a floor surface and angled relative to the first and second plates, wherein the elastic strand nonwoven web is fed under tension underneath the first plate, the second plate and the third plate so that the elastic strand material curls over the third plate and folds over itself on top of the third plate so as to form an elastic strand nonwoven web panel.

According to an exemplary embodiment the second frame member is disposed between the first and second frame members.

According to an exemplary embodiment the one or more rollers comprise: at least two motor driven rollers; and at least one pressure roller disposed between and over the at least two motor driven rollers.

According to an exemplary embodiment the elastic strand material is fed between the at least two motor driven rollers and the at least one pressure roller.

According to an exemplary embodiment the one or more guide rollers angle the elastic strand material away from the unwind module at an angle of 90 degrees relative to a cross-direction of the unwind module.

According to an exemplary embodiment the at least one nonwoven web comprises two nonwoven webs, and the lamination device comprises an ultrasonic horn and anvil configured to entrap the elastic strand material between the two nonwoven webs.

According to an exemplary embodiment the lamination device comprises at least one glue head configured to apply adhesive to at least one of the elastic strand material or the at least one nonwoven web.

According to an exemplary embodiment the system further comprises a vibrator that vibrates the first plate.

According to an exemplary embodiment the third plate expands outwards from the first and second plates towards a distal end portion of the third plate.

According to an exemplary embodiment the system further comprises a vision system configured to identify broken elastic strands, the vision system comprising: a camera; a light source; a monitor operatively connected to the camera; and one or more computers operatively connected to the camera and comprising one or more processors and one or more non-transitory computer readable memories operatively connected to the one or more processors and having stored thereon machine-readable instructions that, when executed by the one or more processors, cause the one or more processors to perform a method comprising: detecting one or more broken elastic strands as illuminated by the light source and imaged by the camera; and generating an alert regarding the one or more broken elastic strands.

According to an exemplary embodiment of the present invention, a method of manufacturing elastic strand nonwoven panels comprises: feeding elastic strand material from an unwind module to a lamination module, the step of feeding elastic strand material comprising: feeding the elastic strand material from one or more cores of elastic strand material disposed on a first frame member to one or more rollers disposed on a second frame member; and feeding the elastic strand material from the one or more rollers to one or more guide rollers on a third frame member that angle the elastic strand material away from the unwind module towards the lamination module; attaching the elastic strand material to at least one nonwoven web at the lamination module to form an elastic strand nonwoven web; and folding the elastic strand nonwoven web over itself at a folding module to form an elastic strand nonwoven panel.

According to an exemplary embodiment the step of attaching the elastic strand material to the at least one nonwoven web comprises ultrasonic bonding.

According to an exemplary embodiment the step of attaching the elastic strand material to the at least one nonwoven web comprises application of adhesive to at least one of the at least one nonwoven web or the elastic strand material.

According to an exemplary embodiment the folding module comprises a first plate, a second plate attached to and extending at an angle relative to the first plate, and a third plate extending substantially parallel to a floor surface and angled relative to the first and second plates, and the step of folding comprises feeding the elastic strand nonwoven web under tension underneath the first plate, the second plate and the third plate so that the elastic strand nonwoven material curls over the third plate and folds over itself on top of the third plate so as to form an elastic strand nonwoven web panel.

BRIEF DESCRIPTION OF THE DRAWINGS

The present invention will be better understood when read in conjunction with the appended drawings. It should be understood, however, that the invention is not limited to the precise arrangements shown. In the drawings:

FIG. 3 is a perspective view of a lamination module according to an exemplary embodiment of the present invention;

FIGS. 6A and 6B are perspective views and FIG. 6C is a side view of an elastic panel folding module according to an exemplary embodiment of the present invention;

DETAILED DESCRIPTION OF THE PREFERRED EMBODIMENTS

Figure 1:
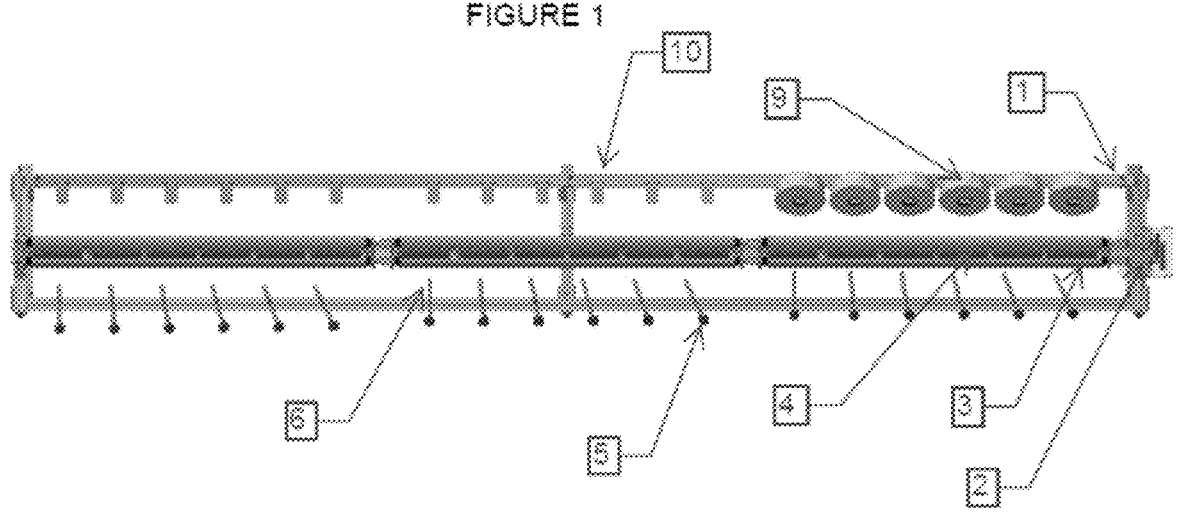
FIG. 1 is a top view of a unwind module according to an exemplary embodiment of the present invention.

FIG. 1 shows an unwind module, generally designated by reference number 10, according to an exemplary embodiment of the present invention. The unwind module 10 is made up of a generally elongate module frame 2 made up of an inner frame member and two outer frame members. One of the outer frame members forms a core stand 1. The core stand 1 may be a bar or rod upon which may be placed one or more cores 9 of elastic strand material. The core stand 1 and module frame 2 may be made from any suitable material such as, for example, plastics, including polyethylene, polypropylene, polycarbonate and the like, metals including stainless steel, aluminum and the like, and combinations thereof.

The inner frame member of the module 10 includes motor driven rollers 3 and pressure rollers 4, with each pressure roller 4 disposed on top of and between two motor driven rollers 3. The rollers 3, 4, may range in length from 6 inches to 60 inches and have a diameter of from 2 inches to 12 inches. The rollers 3, 4 may be made from any suitable material such as, for example, plastics, metals and combinations thereof. Suitable plastics include polyethylene, polypropylene, polycarbonate, polyurethane and the like. Suitable metals include stainless steel, aluminum, and the like. The rollers are round, and run concentric to their center axes to ensure even surfaces and a smooth point of contact. The rollers may be coated with a material to reduce friction such as silicon and the like. If the rollers are made of a semisoft metal such as aluminum, a protective coating, for example a hard coating, may be applied.

Figure 2A:
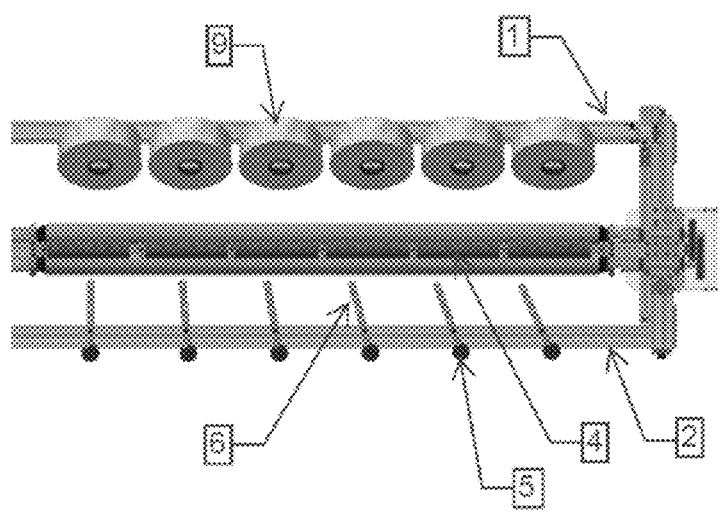
FIGS. 2A, 2B, 2C and 2D are top, side and perspective views, respectively, of an unwind module according to an exemplary embodiment of the present invention.
Figure 2B:
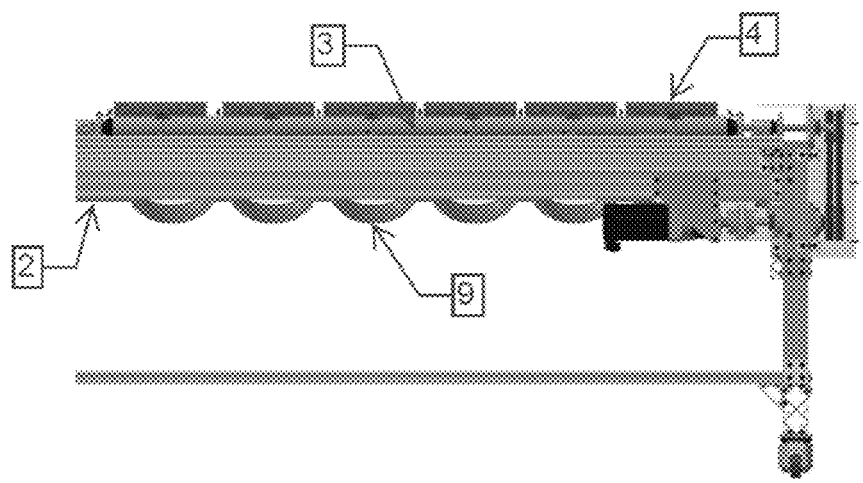
Figure 2C:
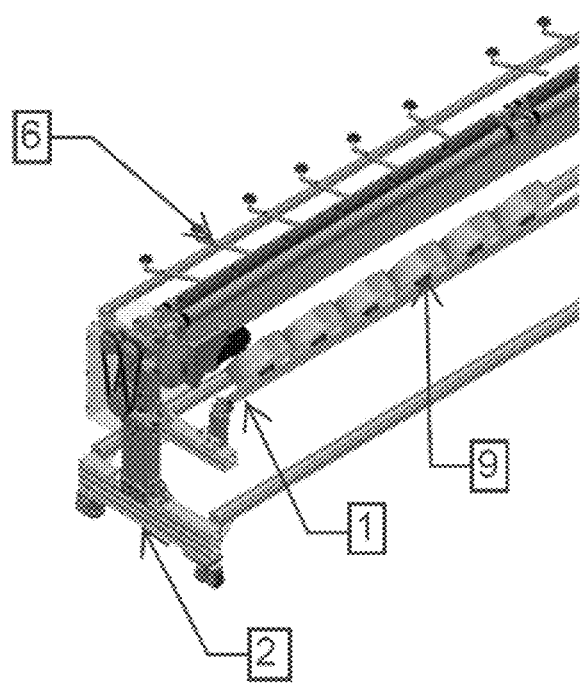
Figure 2D:
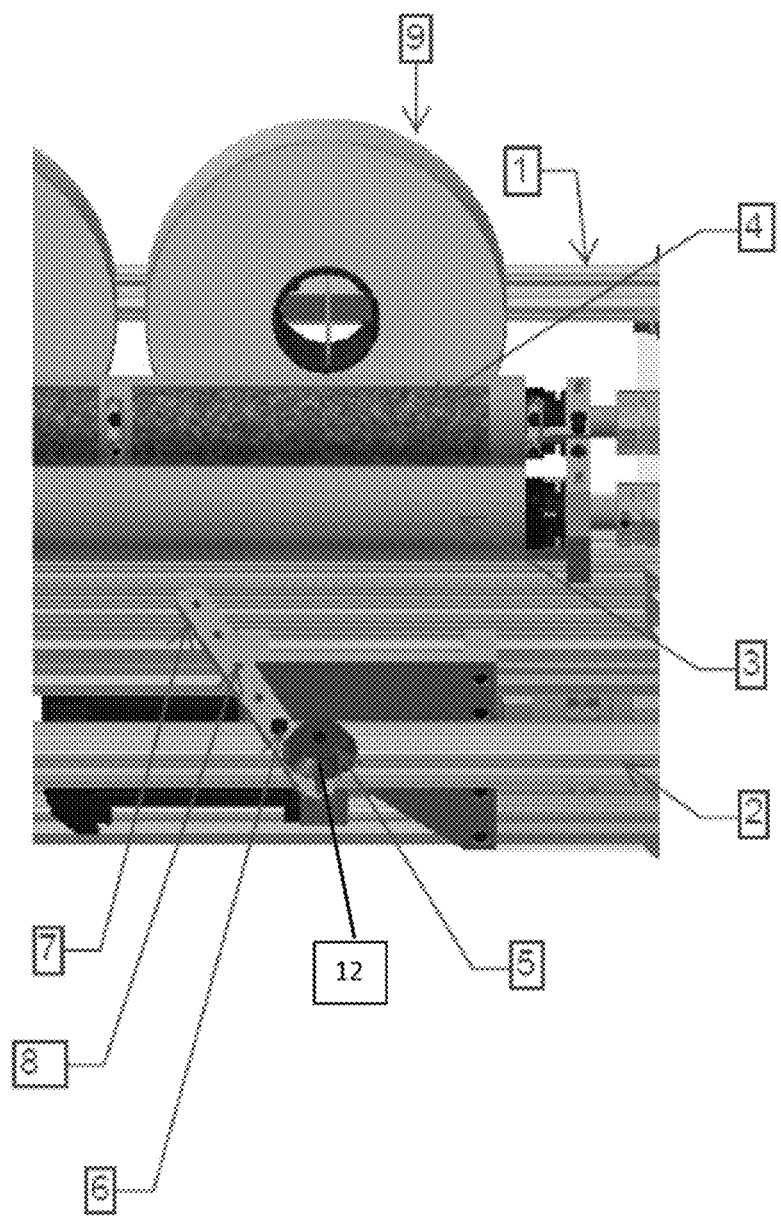

At least one yarn guide roller 5 is attached to the module 10 at the other outer frame member. The yarn guide roller 5 is made up of a bar and a roller member 12 disposed at a distal end portion of the bar 7. The bar 7 is pivotally attached to the outer frame member at a pivot point 6. The yarn guide roller 5 freely spins about the pivot point 6. Suitable pivot points include metal parts assembled in a way to ensure a strong support. As shown in FIG. 2D, pivot point 6 may be made up of a screw that is inserted into one of multiple spaced apart openings 8 along the bar 7. The location of the pivot point 6 may be adjusted along the length of the bar 7 using the openings 8, thereby enabling adjustment of the spacing between elastic strands. The yarn guide roller 5 is attached at a distal end portion of the bar 7. The bar 7 is attached to the module frame 2 through slots 11 in the frame 2. Each yarn guide roller 5 is associated with an individual elastic strand.

In operation, the module 10 may be placed on an aluminum frame having a length of, for example, about 4 feet to about 22 feet and a width of, for example, about 1 foot to about 3 feet. The frame may be on rolling wheels. From about two to about eighteen cores of elastic strands may be placed side by side on the core stand 1. Suitable elastic strands include but are not limited to polyether-polyurea copolymers such as spandex, LYCRA® or elastane. Adjacent the core stand 1, the motor driven rollers 3 and pressure rollers 4 are aligned side by side along the length of the frame, with a set of two motor driven rollers 3 and one pressure roller 4 per elastic strand. Each elastic strand is fed above a respective set of two motor driven rollers 3 and below the respective pressure roller 4 disposed between and on top of the two motor driven rollers 3 and across the width of the frame. Each elastic strand then contacts the respective yarn guide roller 5 (preferably one of the yarn guide rollers 5 disposed most adjacent to the respective set of two motor driven rollers 3 and respective pressure roller 4) where it is turned relative to the width of the frame, then fed directly to a lamination station. In exemplary embodiments, the yarn guide rollers 5 may be configured to turn the elastic strands 90 degrees relative to the width of the frame, or some other suitable angle. The yarn guide rollers 5 are attached on pivot points so they can be adjusted to enable each strand to run parallel to the next strand to align with a glue applicator. As is shown in FIG. 2D, the bars 7 are attached by nuts and bolts that go through different holes 8 along the length of the bars 7 and the slots in the frame 2 to adjust the space between the elastic strands.

The unwind module 10 significantly reduces friction and strain on elastic strands, resulting in less elastic strand breakage. The unwind module 10 also simplifies the re-stringing process such that an operator can quickly find which strand broke, pull the elastic strand off the respective core and feed the strand through the respective motor driven rollers 3, pressure roller 4 and yarn guide roller 5, then directly to a lamination station. This results in the machine only being down for about 5 to 10 minutes as opposed to 20 to 30 minutes compared to conventional systems.

FIG. 3 shows a lamination module, generally designated by reference number 20, according to an exemplary embodiment of the present invention. In exemplary embodiments, the elastic strand unwind module 10 feeds elastic strands to the lamination module 20. A nonwoven may be fed to the lamination module 20 at first input point 21 by, for example, motor driven rollers or any other suitable mechanism. Any motor known in the art may be utilized, such as conventional motors, servo motors and the like. As used herein, "nonwovens" are materials that have not been woven and include, but are not limited to spunbond, spunlace, airlaid materials and extruded materials.

Adhesive is applied to the nonwoven at second input point 22 by, for example, glue head 23 or any other suitable mechanism. Glue flows from a vessel (not shown) through a line (not shown) to the glue head 23 and is applied to the nonwoven. A second glue head 27 applies adhesive to the elastic strands. The second glue head 27 has grooves 24. Each strand 25 is associated with and passes through a respective one of the grooves 24 and is coated with adhesive. Suitable adhesives include hot melt adhesives (e.g., acrylic polymers, block copolymers), emulsion-based adhesives and the like. Dispomelt® and Technomelt® are examples of suitable adhesives available through Henkel AG & Company, KGaA (Dusseldorf, Germany). The amount of adhesive applied may range from 10 to 20 gsm, and may depend on the number of elastic strands.

Elastic strands are fed to the lamination module 20 using the unwind module 10. The number of elastic strands may range from about 2 to about 200. Suitable elastic strands include but are not limited to polyether-polyurea copolymers such as spandex, LYCRA® or elastane. Elastic strands enter the lamination module 20 and travel through grooves in the glue head 27, where adhesive is applied to the strands. The elastic strands travel next into contact with at least one nonwoven and are attached thereto. The adhesive on the elastic strands results in bonding the strands to the nonwovens. Glue head 23 applies glue to the nonwoven in a discontinuous or "on and off" patterns, to prevent blousiness of the nonwoven where elastic strands and related adhesive from the glue applicator 27 are not present based on the desired product design and configuration.

In other exemplary embodiments where there is more than one nonwoven ply, the nonwoven plies and elastic strands may be bonded together using techniques other than application of adhesive, such as, for example, ultrasonic bonding. In this regard, an ultrasonic horn and anvil may be incorporated into the lamination module and may be utilized to entrap the elastic strands between nonwovens. Examples of ultrasonic entrapment are provided in U.S. Pat. No. 6,291,039 and EP 0677284, the contents of which are incorporated herein by reference in their entirety.

The elastic strands are attached to the nonwoven by the adhesive, creating an elastic strand nonwoven that is fed through lamination module 20 towards output point 26. Referring to FIG. 3, the elastic strand nonwoven is fed into a folding module 30. The folding module 30 may be incorporated into the lamination module 20 so that the two modules together may be used to form a single elastic strand nonwoven.

The folding module 30 includes a vibrating inclined folding plate 31, a side angle plate 32 and a folding plate 33. The inclined folding plate 31, side angle plate 32 and folding plate 33 are attached to each other as shown. Vibration may be provided by, for example, vibrators 34 at various cycles/second, depending on the adhesive used, the nonwoven and other factors. An example of a suitable vibrator is a Syntron® vibrator (Syntron Material Handling, Saltillo, Mississippi, USA). The vibrations reduce contact time between the nonwoven and the plate 31, thereby reducing friction and heat and ultimately reducing operating cost. Alternatively, with two or more nonwovens, folding may not be required, or when required, one of the webs may be wider than the other to generate a fold onto itself. The wider nonwoven may also fold over or fold under one of the other nonwovens.

As shown in FIG. 5 and FIGS. 6A, 6B and 6C, the folding module 30 includes the vibrating inclined folding plate 31, the side angle plate 32 and the folding plate 33. The laminated nonwoven web including elastic strands attached to the nonwoven is fed to the folding module 30. In exemplary embodiments, the folding module 30 folds the elastic strand nonwoven over on itself. The amount of fold may range from about 2% to about 50% of the width of the nonwoven 30. The elastic strand nonwoven is folded over on itself as it passes through the folding module 30. The vibrating inclined folding plate 31 is positioned at an angle of about 40° relative to horizontal. The side angle plate 32 (attached to the inclined folding plate 31) is positioned at an angle of about 40° relative to vertical. The folding plate 33 is substantially parallel to a floor surface, set spaced from but in close proximity to the inclined folding plate 31 and its width expands at an angle of about 7° towards its distal end. The length of the folding plate 31 may vary depending on the size of the elastic panel (which may ultimately depend on the size of the diaper or training pant). The present invention is not limited to the angles disclosed herein.

Figure 9:
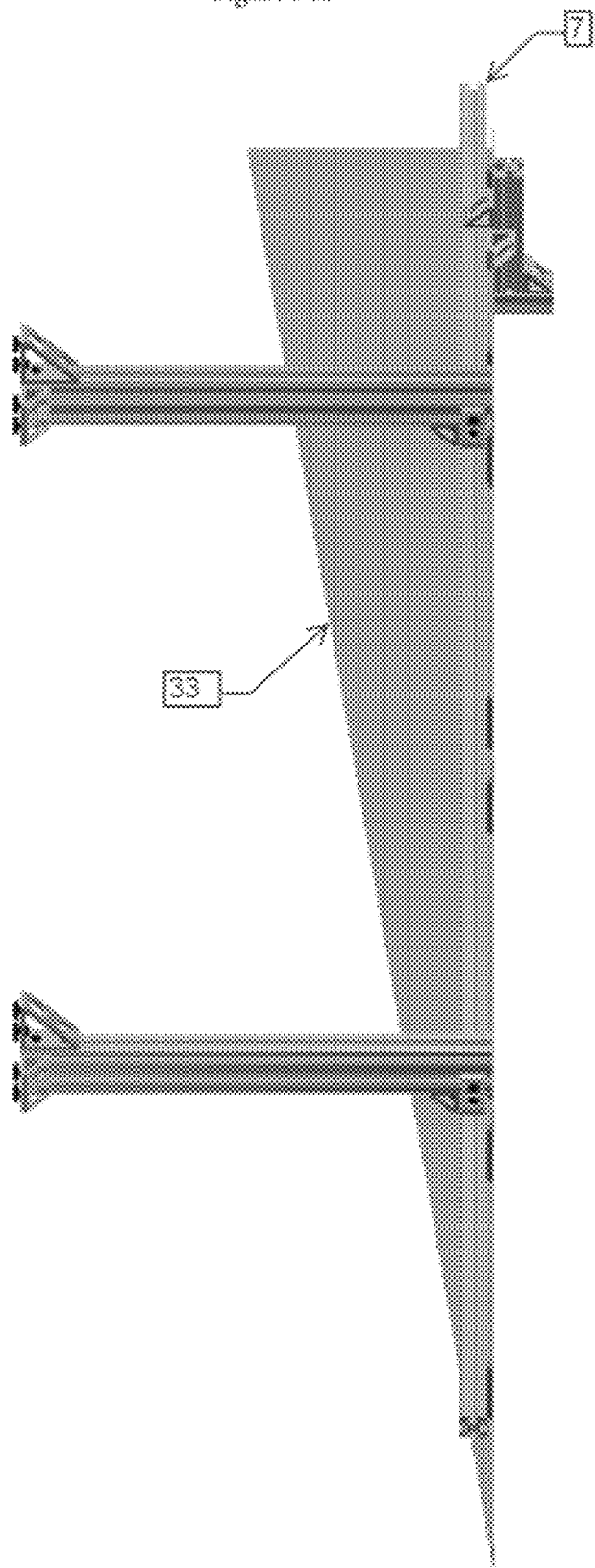
FIGS. 9A-9D show various views of a folding plate according to an exemplary embodiment of the present invention.
Figure 9:
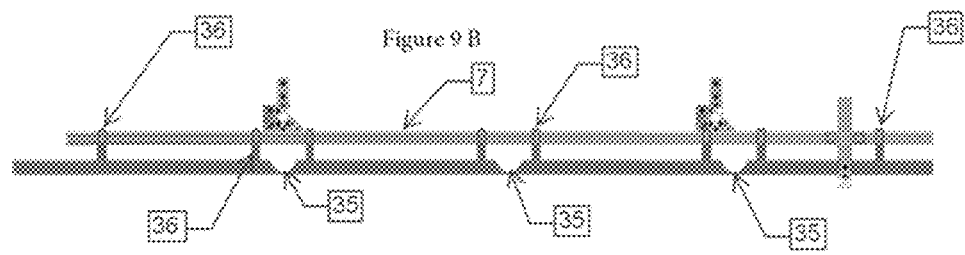
Figure 9:
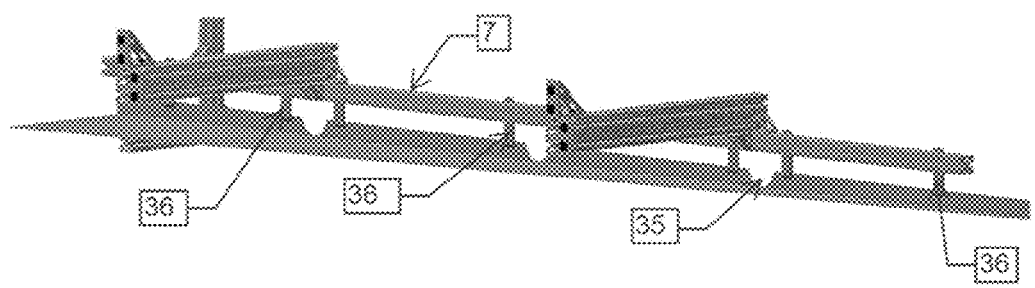
Figure 9:
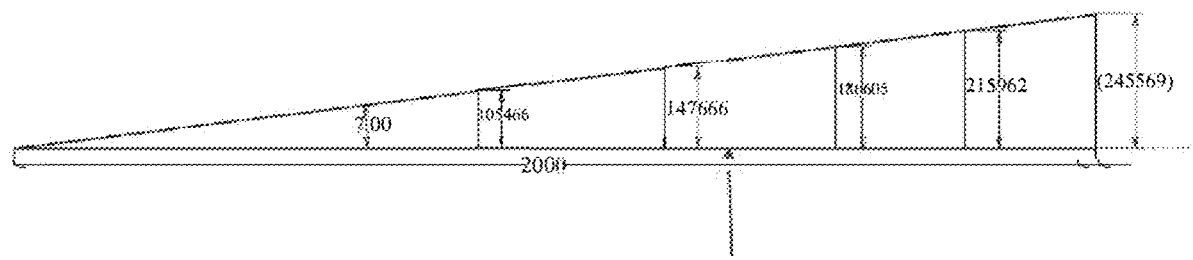

FIG. 9D shows the width of folding plate 33 relative to the length of the plate for one size of elastic panel. In an exemplary embodiment, the folding plate 33 can present a multitude of gradually changing angles with either the middle portion arching up (concave) or down (convex), depending on product configuration. As shown in FIGS. 9A, 9B, and 9C, this can be accomplished by providing the folding plate 33 with notches 35 and adjustable brackets 36. The adjustable brackets 36 may be attached to a frame of the folding plate 33 with a bar 7. Adjustment in length of the adjustable brackets 36 results in bending of the folding plate 33 at the notches 35 and adjustment of the folding plate angle. Attachment of the elastic strands to the nonwoven may continue during the folding process, and the bend in the folding plate 33 gradually enhances such attachment, thereby enhancing the perceived smoothness of the elastic panels. The number of notches may range from 1 to 20 or 2 to 10 depending on the length of the folding plate and materials making up the elastic panel. The number of adjustable brackets may from 1 to 20 or from 2 to 10, depending on the length of the folding plate and the materials making up the elastic panel.

The angles of the plates may vary based on nonwoven material thickness and friction created. The amount of fold over may be varied based on where the nonwoven is positioned as it is fed into the folding module and the design of the folding module. The module may further include means for aligning elastic strands and/or means for observing the elastic strands. Means for feeding a second nonwoven to the module may also be provided. The lamination module may further include means for aligning elastic strands 40.

In operation, the laminated nonwoven web is fed underneath and in contact with the vibrating inclined folding plate 31, the side angle plate 32 and the folding plate 33. As shown in FIG. 6B, for example, the folding plate 33 is positioned to one side (e.g., the right side as shown in FIG. 6B as viewed in the machine direction) of the folding module 30. As the web travels along the folding plate 33, the web is pulled inwards towards and curls on top of the inner edge of the folding plate 33 (i.e., the left side of the folding plate 33 as viewed in the machine direction), resulting in the web folding over itself on top of the folding plate 33. During the folding operation, the elastic strand material remains flat, and the folding operation results in a portion of the elastic strand nonwoven material without the elastic strand material folded over a portion of the elastic strand nonwoven material with the elastic strand material. With the folding plate 33 positioned to the right side as shown in FIG. 6B, this results in a right-side fold line in the web. Without being bound by theory, it is believed that tension applied to the web as it travels below and in contact with the vibrating inclined folding plate 31, the side angle plate 32 and the folding plate 33 results in forces applied to the web that in turn results in the curling/folding of the web onto the top of the folding plate 33. In exemplary embodiments, the folding plate may be positioned on the left side of the folding module 30, resulting in a left side fold line in the web.

Figure 4:
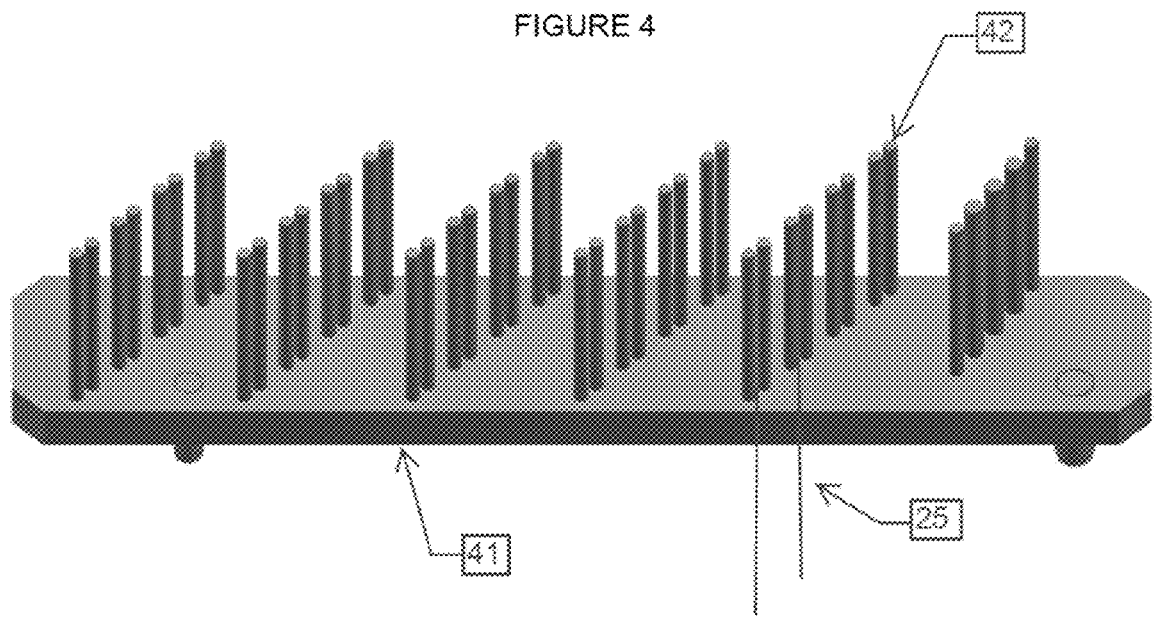
FIG. 4 is a perspective view of a pin guide block according to an exemplary embodiment of the present invention.
Figure 5:
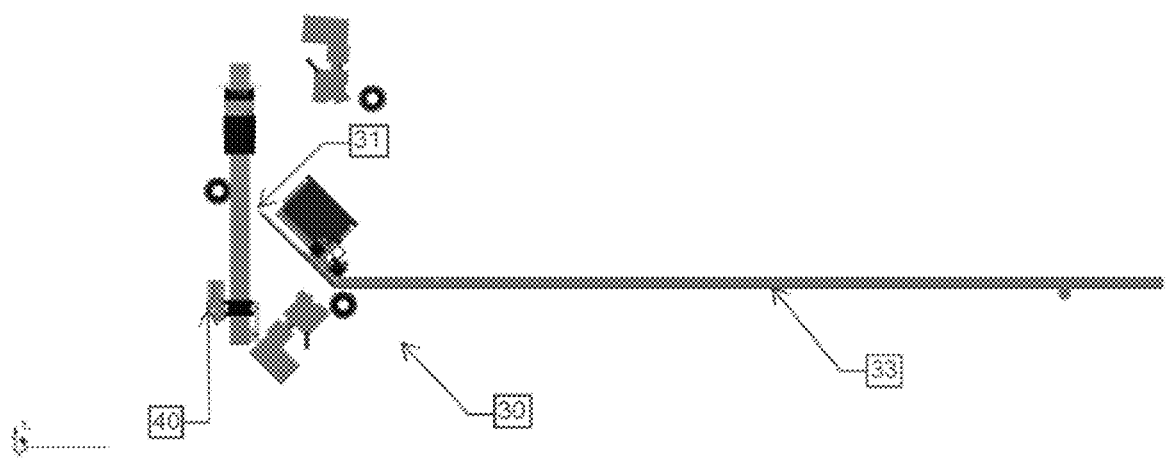
FIG. 5 is a side view of an elastic panel folding module according to an exemplary embodiment of the present invention.

As shown in FIG. 3, in order to have equal spacing between elastic strands, a pin guide block 41 may be placed in front of the lamination module 20. FIG. 4 shows the pin guide block 41 in more detail. The pin guide block 41 includes staggered pins 42, and the elastic strands 25 are fed through the staggered pins 42. Each single elastic strand is fed between two adjacent pins 42, creating zero gap in the cross direction. The number of pins 42 may vary according to the number of elastic strands, but typically varies from 3 to 201. The pin guide block 41 may be removable and may be moved manually by the operator, in instances where many or all elastics needs to be sorted out and aligned where needed, for example to start after a change over. Alternatively, the pin guide block 41 may be moveable through automation, such as through the use of a motor.

It is known to detect the presence or lack of elastic strand(s) by utilizing friction sensors, such as tension controls. Other methods involve detection of the rotation of yarn wheels, which are driven by the elastic strand being fed into the converting process. In exemplary embodiments, the present invention may include a vision system to detect presence of the elastic strands, which removes any friction and rotation of excessive parts.

FIG. 3 shows a vision system, generally designated by reference number 50, incorporated into the lamination module 20. The vision system 50 is configured to observe elastic strands. The vision system 50 may include a camera 51 operatively attached to a monitor 52 and a light source 53. The light source 53 may produce infrared light, white light or other wavelength light to enhance the capability to visualize the elastic strands. The choice of light may vary depending on the location of the module 20. Suitable monitors include devices supplied by the camera's manufacturer, but other means such as a camera feeding a PLC, and consequently, generating the image on an industry standard monitor. Suitable cameras include those commercially available through Cognex Corporation (Natick, Massachusetts, USA), AccuSentry Inc. (Marietta, Georgia, USA) and the like. The camera 51 is preferably on a stand-alone frame so that it does not vibrate, which would otherwise interfere with visualization of the elastic strands. In processes or products where the distance between elastic strands is very small, it is desirable to prevent any primary or secondary vibrations that would cause the smallest fluctuations of strand(s). Alternatively, a control algorithm may be set such that an alarm is triggered when a predetermined average of strand presence is calculated. In a high-speed process, lowering the time scan of detection is not desirable. The means for precisely observing elastic strands allows the process to stop automatically in the event of missing elastic strands. As a result, such detection enables an operator to quickly determine which elastic strand broke and quickly replace the strand. The pin guide block 41 is preferably moveable such that it may be above the camera 51 during stringing elastic strands to the lamination module 20 and moved away during operation such that it does not interfere with the camera 51. An alarm may be provided, which sounds upon detection of elastic strand breakage. Moreover, with the use of strand identification numbers, because the camera 51 can precisely detect each strand, the operator can effectively act upon correcting the missing strand by matching the information from the camera 51 attached to the monitor 52.

Nonwoven web handling processes commonly require turning of the nonwoven web or panel to align with a diaper manufacturing process. This typically requires the web to be re-directed 90 degrees, from the incoming to the outboard direction. A turning rod, generally called a turn bar is utilized to achieve such a requirement. Moreover, to reduce friction generated from the nonwoven web constantly running in contact with the metal turn bar, a surface coating is added to reduce friction. Solid rod turn bars create continuous nonwoven web contact which results in more friction and heat. Prior attempts to address this issue involve the use of hollow turning rods, with compressed air supplied to the rod. For nonwoven elastic strand laminated products, there is a need for an improved turn bar with less friction and associated heat generation.

In exemplary embodiments, the present invention provides an improved turn bar that is suitable for use with porous nonwoven webs with light basis weight, nonwoven webs coated with hot melt adhesive, and machine direction tension generated by multiple elastic strands coated with hot melt adhesive.

A turn bar, or whirling bar, according to an exemplary embodiment of the present invention, includes at least two adjacent rods driven around a common center axis and by a common motor. By having adjacent rods, a nonwoven web passing over the bar assembly and being turned approximately 90 degrees has less contact with the turn bar and therefore creates less friction and heat. In other words, as the nonwoven web or panel makes its way around the center axis, there are multiple small points of contact. The turn bar may have from about 2 to about 14 or from about 6 to about 10 individual rods. Each rod may have a length of from about 0.5 to 6 feet and a diameter of from about 0.25 to about 3 inches. The overall turn bar length may range from about 0.6 to 6.5 feet and the overall diameter of the turn bar may range from about 1 to about 12 inches.

In order to further reduce friction and improve the turn bar performance, the whirling bar of the present invention may be connected to two driving units. The first driving unit is a motor to provide rotation within its center axis. Suitable motors for the first driving unit include a continuous RPM AC, or variable speed unit. The second driving unit provides an oscillating motion, to move the motorized whirling bar assembly left, then right, then left and so on. Suitable motors for the second driving unit include a continuous RPM AC or speed variable unit. The two motions, generally active while the process is running, and desirably above certain linear speeds, limits the amount of time the web makes contact with the turn rods. This limited interaction between the nonwoven web or panel and the rods can drastically reduce heat generated by friction and contamination.

The whirling bar rods may be made of any suitable material including a variety of metals such as stainless steel, aluminum and the like, or nonmetals such as plastics. The rods need to maintain a certain rigidity and may not be too flexible. Moreover, depending on the material, an auxiliary coating may be applied to the rods to reduce friction or enhance the smooth surface of the rods. The rotation around the central axis, as well as the oscillating motion speeds, can be varied depending on the process. Although the utility of the turn bar is demonstrated with nonwoven web panel manufacturing, the turn bar may be suitable for a variety of applications.

A vibrating unit may be connected between the multi-rod turn bar and its mounting system. This high frequency motion drastically reduces the dwell time the nonwoven web or panel is in contact with the rods during standard operation.

In another exemplary embodiment, the rods surrounding the center axis rotate within their own axis, while the entire assembly is also rotated.

Figure 7:
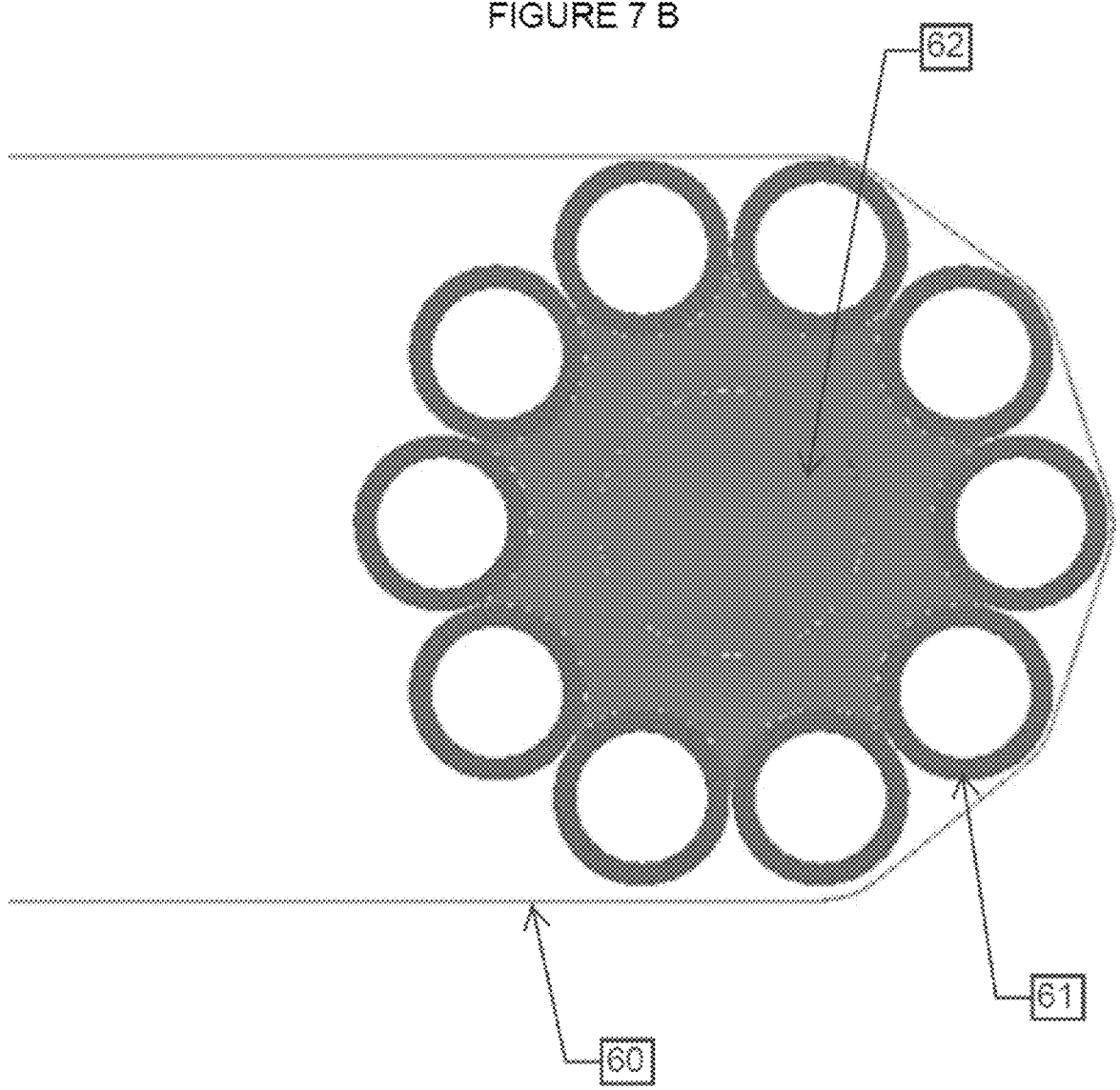
FIGS. 7A and 7B are perspective and cross-sectional views, respectively, of a turn bar according to an exemplary embodiment of the present invention.

FIGS. 7A and 7B show a turn bar, generally designated by reference number 60, according to an exemplary embodiment of the present invention. As shown, the turn bar 60 includes multiple rods 61 about a central axis 62. The rods rotate so that transverse motion may be provided.

Prior to the turn bar, the elastic strand nonwoven material may be fed through a deactivation module where portions of the elastic strand material are cut and the nonwoven material at the cut points remain held together by adhesive previously applied to the nonwoven at the lamination module. Examples of such deactivation processes are described in U.S. Pat. Nos. 5,707,470 and 5,643,396, the contents of which are incorporated herein by reference in their entirety.

Figure 8:
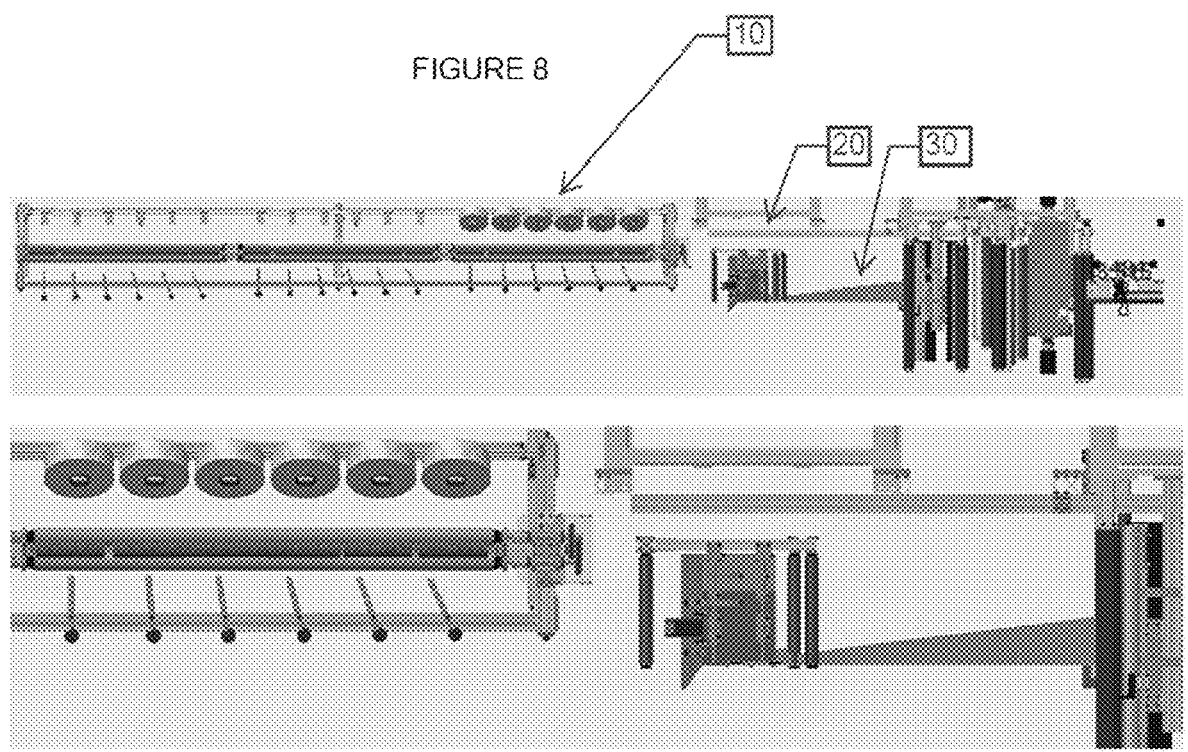
FIG. 8 is a representative diagram of a system for making elastic laminates according to an exemplary embodiment of the present invention.

FIG. 8 shows a system for manufacturing elastic strand nonwoven panels, generally designated by reference number 100, according to an exemplary embodiment of the present invention. The system 100 includes a combination of the unwind module 10, the lamination module 20 and the folding module 30. In order to reduce floor space required for a diaper manufacturing machine and associated modules, elastic unwind modules, lamination modules and folding modules may be built on a mezzanine above a diaper manufacturing machine. By building the elastic unwind module, lamination module and folding module above the diaper manufacturing machine, an optimum web path for the multitude of elastic strands to enter the nonwovens webs on the same parallel configuration is created.

The following examples are for illustrative purposes. The claims are not limited to the details thereof.

Example 1

An elastic strand unwind module was built with a configuration as described herein. Core stands and a module frame were made of aluminum parts. There were 18 core stands. The motor driven rollers were made of hard coated aluminum thin wall tubing and measured 73.25 inches long with a diameter of 2.93 inches. The motor was a Servo B4540 from Rockwell. The yarn guide rollers were A612030 from YUASA. The yarn guide rollers were attached to the frame with a bolt, spacer and mounting pivot plate which was able to pivot at an angle ranging from 0 to 90 degrees. The pressure roller was made of abrasion resistant polyurethane rubber round tube and measured 11.5 inches long and had a diameter of 2.5 inches OD by 1.5 inches ID. A pin guide box having 45 pins spaced in a staggered configuration to achieve for example, multiple pitches of 8.3 mm apart, and multiple pitches of 4 mm apart was placed down-stream from the yarn guide rollers and in front of a lamination module and a folding module. The pin guide box was on a track. A glue head applied intermittent strips of construction adhesive to the nonwoven. The glue head to apply adhesive to the elastic strands was from Nordson Corporation (Westlake, Ohio, USA). The camera was from Cognex. The monitor was from Cognex. The inclined folding plate was set at an angle of 40° relative to the folding plate. The side angle plate was set an angle of 40° relative to vertical. The folding plate was substantially parallel to the floor and its width expanded at an angle of 7° moving away from where it was attached to the inclined folding plate. The length of the folding plate was 66 inches. Vibration was provided by Syntron Material Handling (Mississippi, USA). A 10 gsm spunbond nonwoven from PFN company was fed to the lamination station and coated with TECHNOMELT DM 901M at 3 gsm construction adhesive, with the adhesive temperature ranging from 300 to 320 F, zone dependent (type/temperature). Fourteen (14) elastic strands of a first type (Lycra 540 dTex), and four (4) elastic strands of a second type (Lycra 800 dTex) were fed to the lamination module from the elastic unwind and attached to the nonwoven. The elastic nonwoven was passed through the folding module, which resulted in the elastic nonwoven folding over on itself, creating an elastic panel. The width of the elastic nonwoven was 400 mm. The width of the elastic panel was 200 mm.

Example 2

The modules of Example 1 were used with a second nonwoven feed. The first nonwoven was a 15 GSM, 240 MM wide. The second nonwoven was a 10 GSM, 170 MM wide. The nonwovens were fed to the lamination module where, in this case, the wider NW was zone intermittently coated with construction adhesive. The elastic strands were fed through the pins and then into the grooves of the elastic hot melt applicator, where strands were coated individually. Consequently, the elastic strands were sandwiched between the two layers of nonwoven webs.

Although specific embodiments of the invention have been described above in detail, the description is merely for purposes of illustration. It should be appreciated, therefore, that many aspects of the invention were described above by way of example only and are not intended as required or essential elements of the invention unless explicitly stated otherwise. Various modifications of, and equivalent steps corresponding to, the disclosed aspects of the exemplary embodiments, in addition to those described above, can be made by a person of ordinary skill in the art, having the benefit of this disclosure, without departing from the spirit and scope of the invention defined in the following claims, the scope of which is to be accorded the broadest interpretation so as to encompass such modifications and equivalent structures.

The invention claimed is:

1. A method of manufacturing elastic strand nonwoven panels comprising:
   A. feeding elastic strand material from an unwind module to a lamination module, the step of feeding elastic strand material comprising:
      i. feeding the elastic strand material from one or more cores of elastic strand material disposed on a first frame member to one or more rollers disposed on a second frame member; and
      ii. feeding the elastic strand material from the one or more rollers to one or more guide rollers on a third frame member that angle the elastic strand material away from the unwind module towards the lamination module;
   B. attaching the elastic strand material to at least one nonwoven web at the lamination module to form an elastic strand nonwoven web; and
   C. folding the elastic strand nonwoven web over itself at a folding module to form an elastic strand nonwoven panel, the folding module comprising a first plate that is a vibrating inclined folding plate, a second plate attached to and extending at an angle relative to the first plate, and a third plate extending substantially parallel to a floor surface and angled relative to the first and second plates, and the step of folding comprising feeding the elastic strand nonwoven web under tension underneath the first plate, the second plate and the third plate so that the elastic strand nonwoven web curls over the third plate and folds over itself on top of the third plate so as to form the elastic strand nonwoven web panel.

2. The method of claim 1, wherein the step of attaching the elastic strand material to the at least one nonwoven web comprises ultrasonic bonding.

3. The method of claim 1, wherein the step of attaching the elastic strand material to the at least one nonwoven web comprises application of adhesive to at least one of the at least one nonwoven web or the elastic strand material.

4. The method of claim 1, wherein the second plate extends at the angle relative to the first plate so that the second plate extends upwards relative to the first plate.

* * * * *